United States Patent [19]
Weinmann

[11] Patent Number: 5,240,010
[45] Date of Patent: Aug. 31, 1993

[54] FERTILITY PROBE

[76] Inventor: Joseph Weinmann, 6 Rashba Street, Jerusalem, Israel

[21] Appl. No.: 830,376

[22] Filed: Jan. 31, 1992

[30] Foreign Application Priority Data

Jan. 31, 1991 [IL] Israel .................................. 97115

[51] Int. Cl.$^5$ .............................................. A61B 5/05
[52] U.S. Cl. ...................................... 128/734; 128/738; 364/413.12
[58] Field of Search ............... 128/738, 734, 736; 364/413.02, 413.05, 413.12

[56] References Cited

U.S. PATENT DOCUMENTS

| | | | |
|---|---|---|---|
| 4,148,304 | 4/1979 | Mull | 128/738 |
| 4,224,949 | 9/1980 | Scott et al. | 128/734 |
| 4,328,809 | 5/1982 | Hirschowitz et al. | 128/653 |
| 4,465,077 | 8/1984 | Schneider | 128/738 |
| 4,498,481 | 2/1985 | Lemke | 128/734 |
| 4,577,640 | 3/1986 | Hofmeister | 128/738 |
| 4,685,471 | 8/1987 | Regas et al. | 128/734 |
| 4,753,247 | 6/1988 | Kirsner | 128/734 |
| 4,771,791 | 9/1988 | Kubouchi | 128/736 |
| 5,137,028 | 8/1992 | Nishimura | 128/738 |

*Primary Examiner*—Max Hindenburg
*Assistant Examiner*—Guy V. Tucker
*Attorney, Agent, or Firm*—Jacobson, Price, Holman & Stern

[57] ABSTRACT

There is provided a method for the determination of the fertile and infertile periods in the monthly cycle of females, and a device for carrying out the measurements and evaluations of this method. The method is based on the measurement of changes of characteristics of the cervical mucus and of polarization impedance. Furthermore, additional auxiliary information can be obtained by daily temperature measurements. A device is provided for effecting the required measurements, and for the evaluation of these.

9 Claims, 8 Drawing Sheets

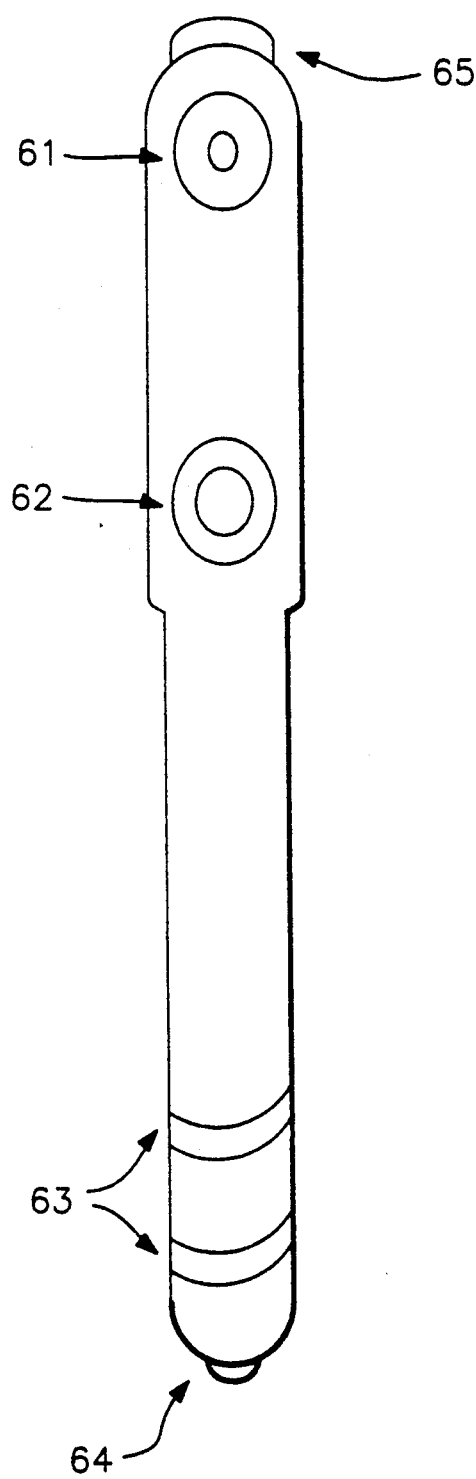
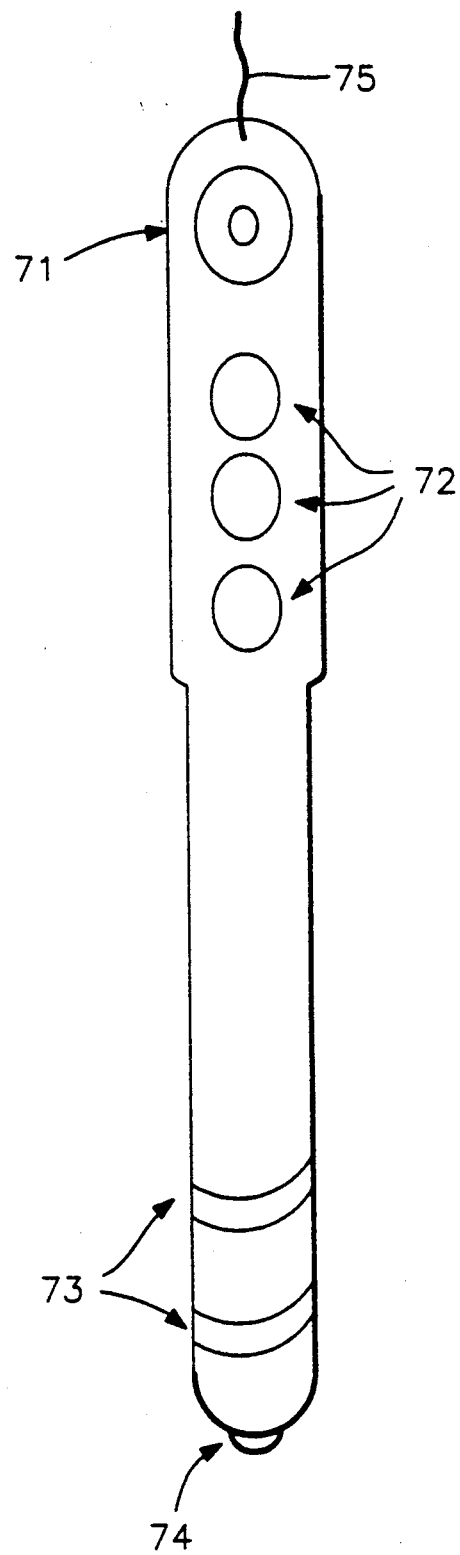

FERTILITY PROBE

FIELD OF THE INVENTION

There is provided a device for determining the fertile and infertile phase in the cycle of a woman. The device measures both the changes of cervical mucus quality which is determined by polarization impedance, as well as changes of temperature during the menstrual cycle. The results of such measurements are evaluated and a signal is provided indicating the fertile and infertile phases of the reproductive cycle.

BACKGROUND OF THE INVENTION:

Various attempts have been made to determine the fertile and infertile periods in women by a variety of electrical measurements. U.S. Pat. No. 4,328,809 relates to a device for detecting the potential level of the electromagnetic field of a living organism, and purports to assess the time of ovulation by measuring the electrical potential difference between index finger, middle fingers and thumbs, the peak levels of potential being supposedly indicative of the occurrence of ovulation. A commercial device termed "Menstrual Cycle Monitor" measures ionic changes in saliva and cervical mucus by determining the changes of electrolyte content of these.

A device has been described which makes use of four electrodes, and this is set out in FIG. 1. This is not part of the present invention and was the first attempt by the inventor to measure changes in electrical resistance in the vaginal walls of a woman to determine ovulation. In the four-electrode technique, a high frequency current of the order of several tens of KHz of a known intensity (tens of $\mu A$) is sent through the electrodes 1 to 4 into the vaginal wall. Electrodes 2 and 3 are connected to an amplifier which has a very high input resistance, of the order of hundreds of Meg-ohms Due to its high input resistance the amplifier measures the voltage V across the electrodes 2 and 3, without drawing practically any current, and therefore the impedance of the metal/tissue interface which is a function of the current flowing through it, and interferes with the tissue resistance measurement can be neglected. Thus, the measured voltage V equals $I \times R$, where I is the known current and R is the resistance of the vaginal wall stretch between the electrodes 2 and 3. Thus R can be calculated as V/I.

FIG. 1 illustrates a four-electrode probe marketed by ZETEC, which is intended to detect the fertile period in the cycle of a woman. This is termed "VER" (Vaginal Electrical Resistance) Method. This seems to be based on an earlier development by the inventors of the present invention.

U.S. Pat. No. 4,753,247 purports to measure the same phenomena, but by means of another parameter—a minimum of admittance—which is measured by means of semiconductor electrodes. The frequencies used according to that U.S. Patent are lower by an order of magnitude, and according to FIGS. 9 and 10 the DC and AC currents are superpositioned. Furthermore, the results reported in the U.S. patent show that lowest admittance was measured on the 12th day of the cycle at 1 KHz frequency, and on the 17th day with a frequency of 10 KHz. According to the present invention the 16th day is pinpointed by the actual measurements. The 12th day and 17th day results are clearly not acceptable as they fail to indicate the critical period of ovulation The above is clearly evident from FIG. 5 of the said U.S. Patent.

According to the present invention the four-electrode probe and the above method of measurement has been abandoned, as the present invention provides simplified yet more accurate and reliable means for predicting the fertile and infertile phase in the cycle of a woman.

BRIEF DESCRIPTION OF THE DRAWING

The invention is further illustrated by means of the following schematical Figures, not according to scale, graphs, block diagrams and wiring diagrams, in which:

FIG. 6 is a perspective view of a probe for hospital use;

FIG. 7 is a perspective view of a probe for domestic use;

DETAILED DESCRIPTION OF THE PREFERRED EMBODIMENT

Figure 3:
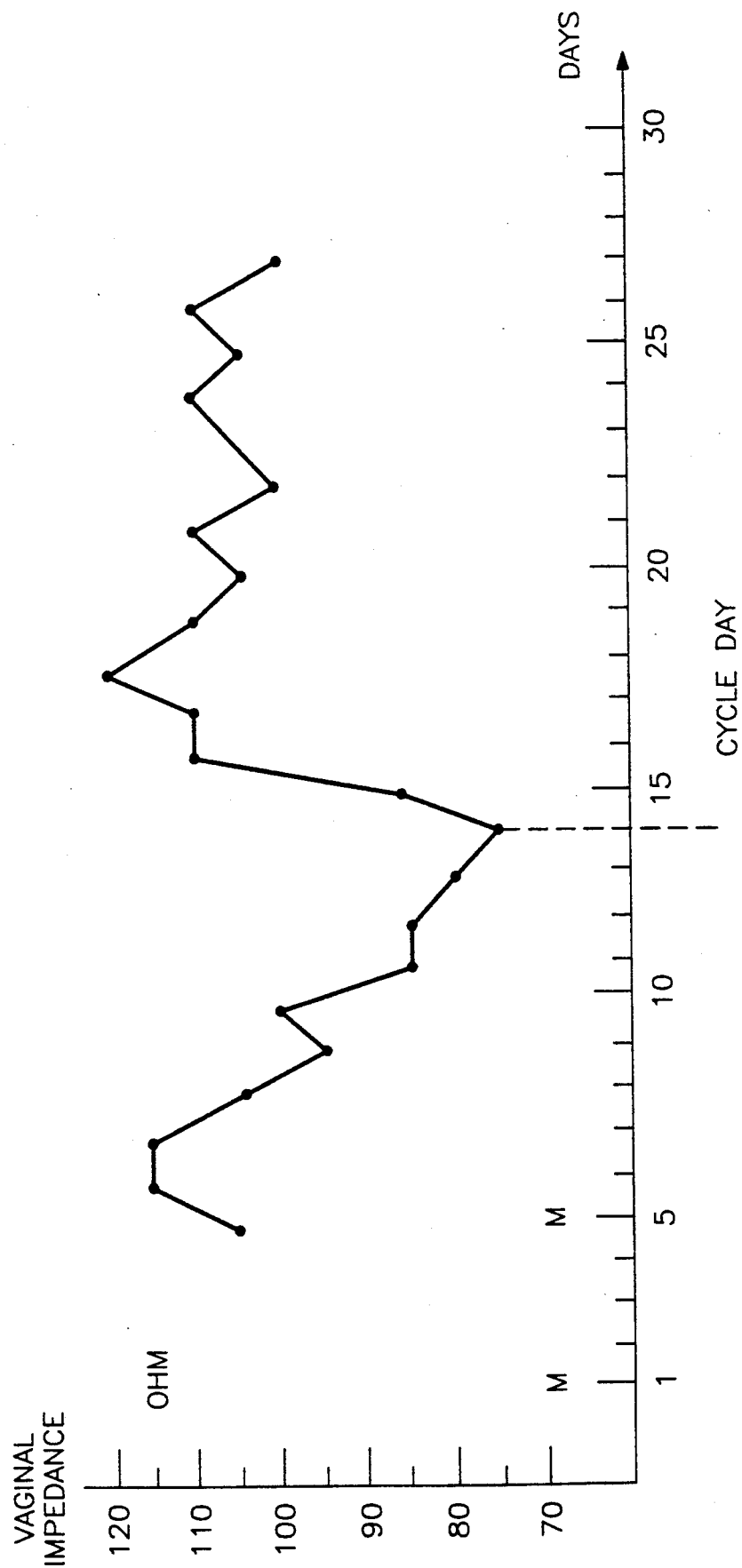
FIG. 3 is a graph of polarization impedance measurements over the entire monthly cycle.

According to the present invention means are provided for an accurate prediction of approaching ovulation by monitoring changes in cervical mucus secretion by the use of a vaginal probe with two electrodes only located close to the tip of the probe and thus near the entrance of the cervix. The two electrodes ar covered during the measurement by the mucus secreted by the cervical glands which descends into the vagina. A high frequency current of I is sent through the two electrodes into the vagina. This current is carried by electrons via the metal conductors and via ions in the mucus, resulting in an interface impedance Z. The voltage drop V across Z is $I \times Z$. V is measured by a simple amplifier connected with the two electrodes and from V it is possible to calculate Z as V / I. With approaching ovulation, secretion of cervical mucus increases and the interface polarization impedance Z decreases and measurements carried out on a daily basis result in a graph, such as shown in FIG. 3.

For simplicity the variable measured named "vaginal impedance" is used, even as in reality the variable measured is the polarization impedance of the Metal Electrode/Cervical Mucus Interface.

Figure 1:
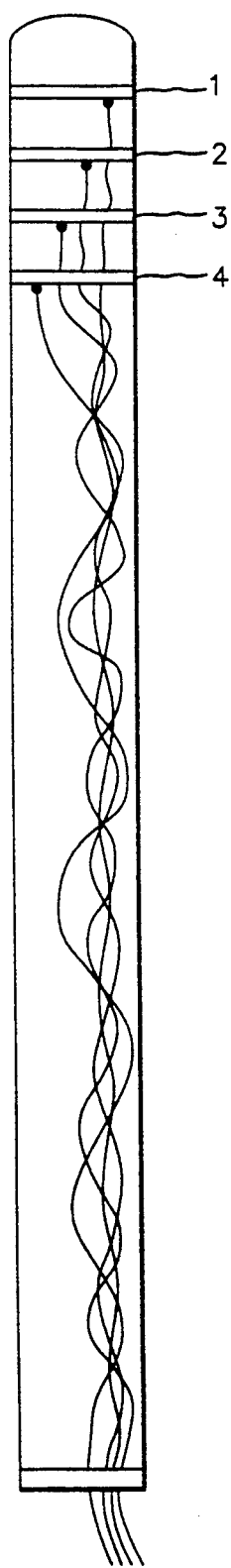
FIG. 1 is a side view of a commercial device according to the prior art.
Figure 5:
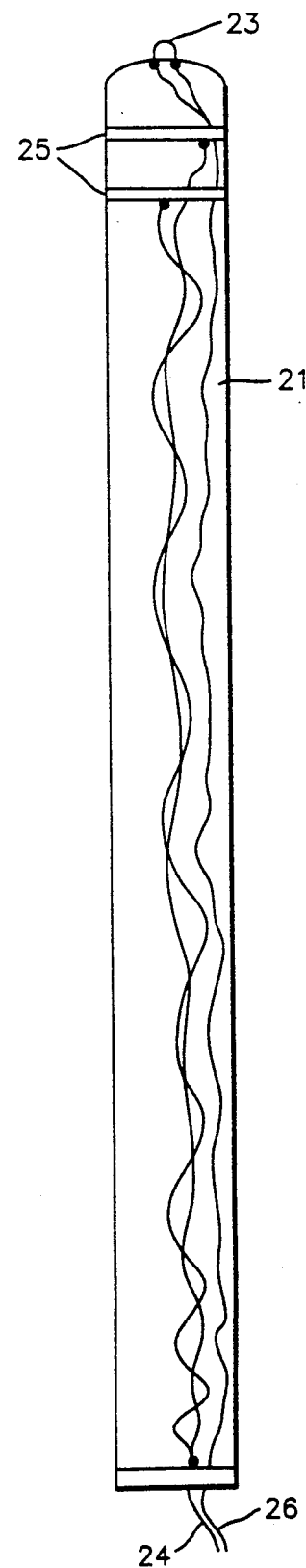
FIG. 5 is a schematical side view of a probe according to the invention.

A device of the invention is illustrated schematically in FIG. 5, where 21 is the body of the probe, 25 are the two electrodes and 24 and 26 are the leads leading from the two electrodes, respectively. The probe with the two electrodes enables a much higher dynamic range of the measurements and the results which are achieved using this probe are more accurate than those which were achieved with the four-electrode probe. It is also simpler, cheaper for manufacture and also the electronics needed is simpler and considerably less expensive.

It is advantageous to combine the measurement of the impedance with a measurement of the basal body temperature (BBT) of the woman examined. It has been known that there exists also a correlation of this parameter with the process of ovulation and the combined evaluation of both parameters provides increased accuracy and re liability in the determination of the fertile and infertile phases of the menstrual cycle as they were monitored during the field tests. In order to make it even more powerful, the rhythm method formula is also integrated into the software of the device as support for unpredicted changes which might occur due to irregularity of the menstrual cycle.

A device according to the invention for measuring both electrode polarization impedance as well as temperature is illustrated with reference to FIG. 2, in which 11 is a probe adapted to be inserted into the vagina; which probe contains electrodes 12 and 13, at a certain distance from each other, one of which, 12 and 13 is connected to a 500 Hz to 100 KHz current source 14, and to amplifier 15, the second being connected to the amplifier 15 via wire 17.

This amplifier 15, is connected to rectifier 18 which is connected to dual-input A/D converter or V/F converter 19, which is also connected with the temperature sensor 20 in probe 11 via signal conditioner 21. The A/D or V/F converter 19 is connected with Digital Processor 22 and to display 23. The digital processor 22 computes the relevant data based of an algorithm relating to the impedance measurement by the probe 11 when mucus 24 is between the two electrodes 12 and 13, and on the temperature measurements by sensor 20. The input is passed via two distinct channels and computed separately, the results being used to provide the desired information, which is used to actuate the display which can be by way of LCD color-LED or by an audio signal or both.

According to a preferred embodiment of the invention the probe carries also accurate temperature measuring means, and the results of the two measured parameters ar integrated to provide a reliable and accurate prediction of the fertile and infertile phases of the menstrual cycle. FIG. 3 illustrates the results of cervical mucus polarization impedance measurements over an entire menstrual cycle, where a clear minimum is observable which is obtained when the electrode polarization impedance is at its lowest level, and the amount of cervical mucus is at a maximum.

Figure 8:
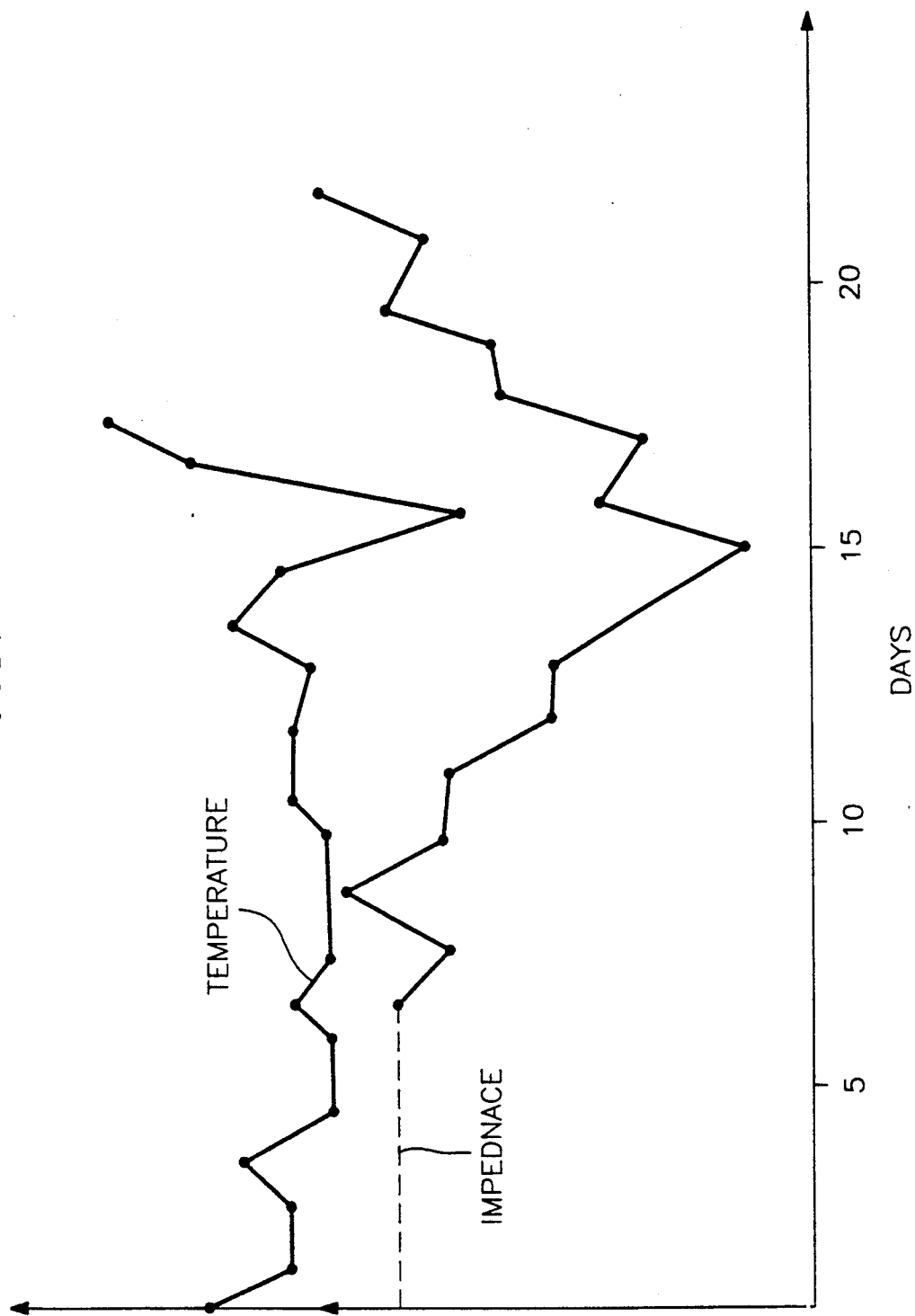
FIG. 8 is a graph or polarization impedance and of temperature measurements over an entire cycle.

A typical graph of such measurements is given in FIG. 8, showing both parameters.

Figure 4:
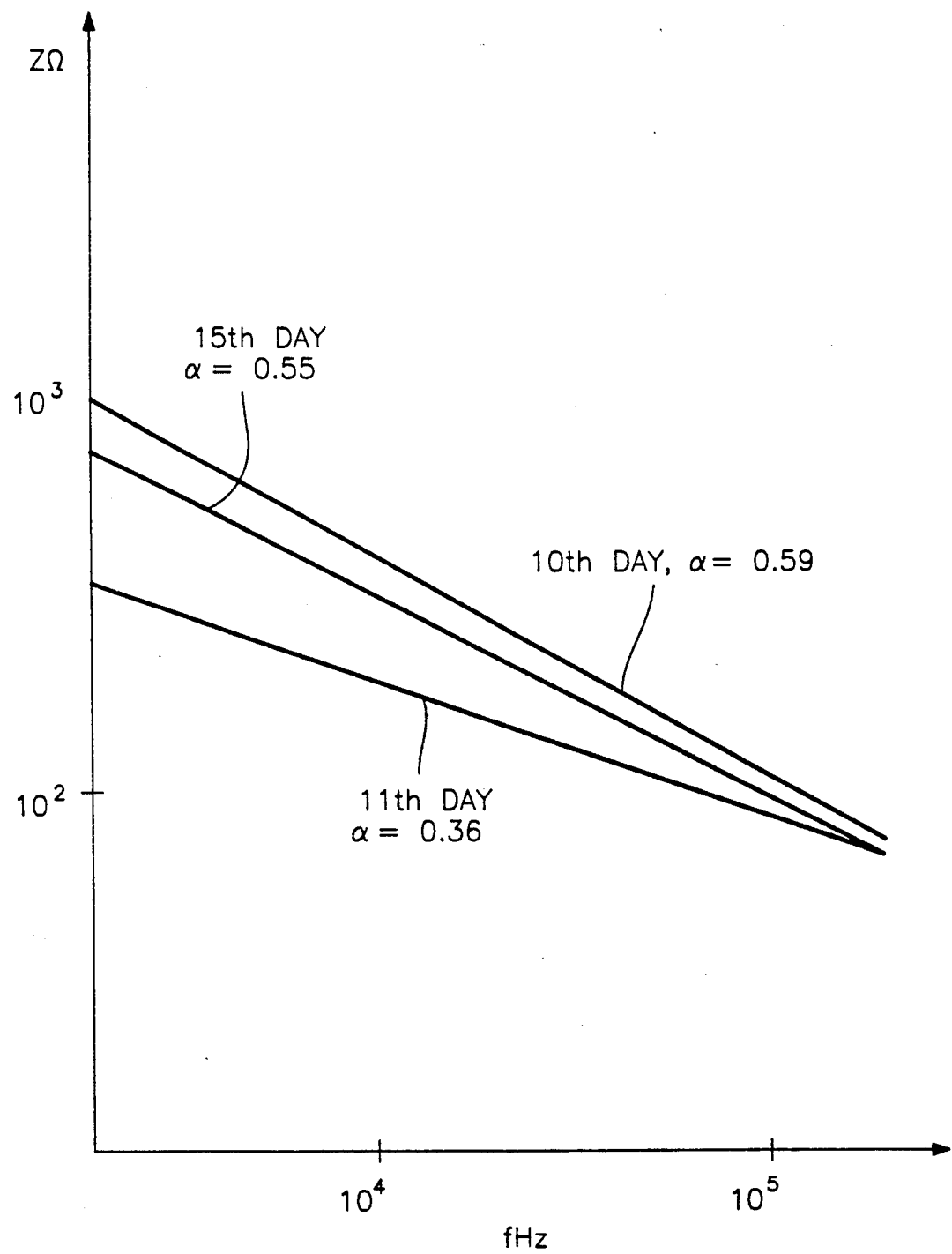
FIG. 4 is a graph of interface polarization impedance measurements.

FIG. 4 demonstrates that the variable monitored by the two-electrode probe is indeed the "Electrode Polarization Impedance". In order to prove this in some subjects daily vaginal measurements with the two-electrode probe were performed at a number of frequencies between 2 KHz and 200 KHZ.

It is known from the electrochemical theory of electrode polarization that on a log/log graph the relationship between Electrode Polarization Impedance Z and the frequency of the measuring current will be a straight line with a slope alpha smaller than 1, as shown in FIG. 4 which illustrates the results of our measurements, and prove that the measured parameter is the electrode polarization impedance.

A device of the invention is illustrated with reference to FIG. 5, which illustrates a probe according to the invention.

FIG. 6, which illustrates a professional version of a probe for hospital or clinical use;

FIG. 7 illustrates a simpler, consumer version of such a device.

Figure 2:
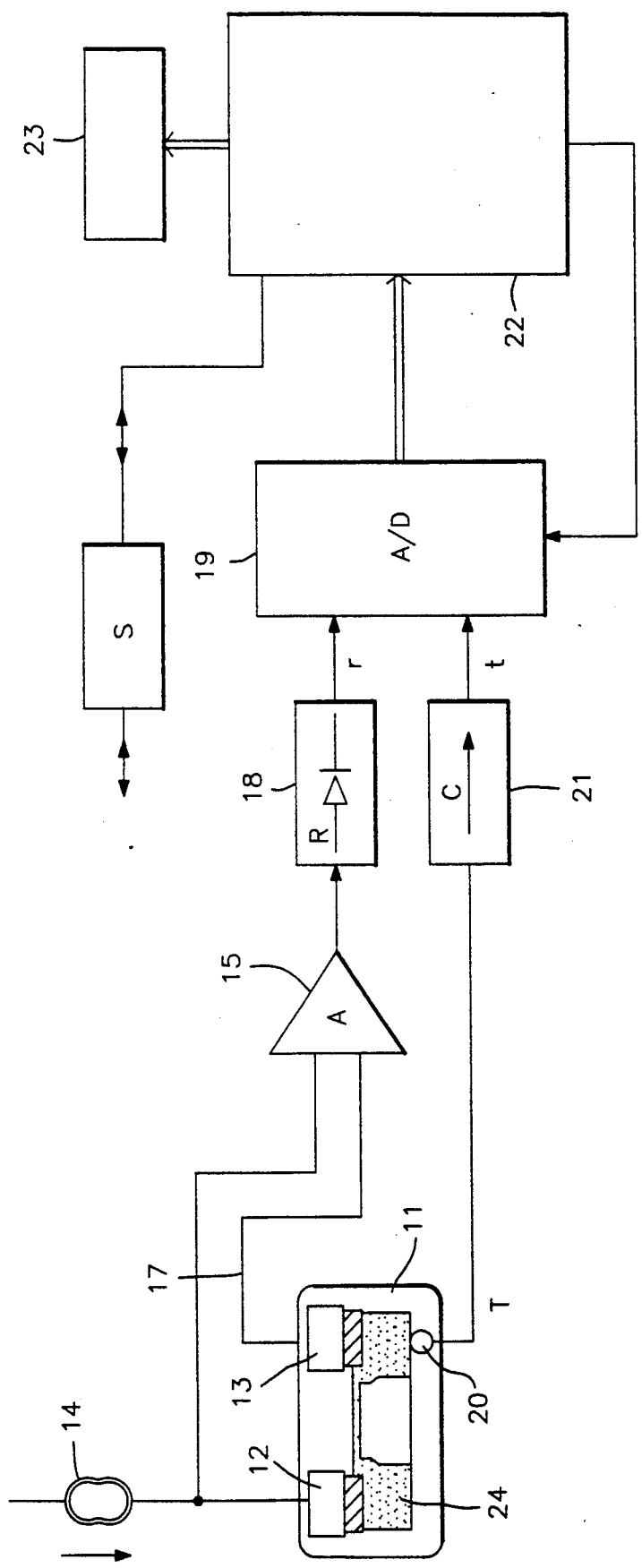
FIG. 2 is a block diagram of a device of the present invention.

As shown in FIG. 2, a probe comprises an elongated member 21, made of non-conductive material at the end of which there are provided two ring-shaped electrodes 25, which are connected via wires 24 to the outside. At the end of the probe, there can be provided a temperature sensor 23 which is also connected via a wires 26 to the outside of the probe.

The procedure is that each morning a measurement is carried out, during about 10–30 seconds, with the data being stored in a microprocessor, and which data are processed according to existing software algorithms, providing a clear indication of the various phases of the cycle. The combined data provides reliable means for recognizing fertile and infertile phases of the cycle. A typical graph of such a measurement of the two parameters is given in FIG. 8.

According to a simplified embodiment of the invention there is provided a system for domestic use. This comprises a probe of the invention, integrated with a microprocessor which will be used to compute daily measurements and to indicate via three difference LEDS or LCD display: (1) a signal indicating that ovulation is approximately three days away; (2) a signal indicating the most fertile period (day) of ovulation; (3) a signal the start of the infertile phase after ovulation. If LEDS are used they are preferably of different color. The entire device is in the form of a compact integrated apparatus housed in the handle of the probe, provided with such indication means.

In FIG. 6 61 is a calibration button, 62 a daily button, 63 the two test electrodes, 64 temperature electrodes and 65 a connector for the P.C. computer;

In FIG. 7, 71 is a calibration and daily button, 72 are the respective yellow, red and green LEDs, 73 are the two test electrodes and 74 the temperature electrodes, 75 being a connector to the P.C. computer.

Figure 9:
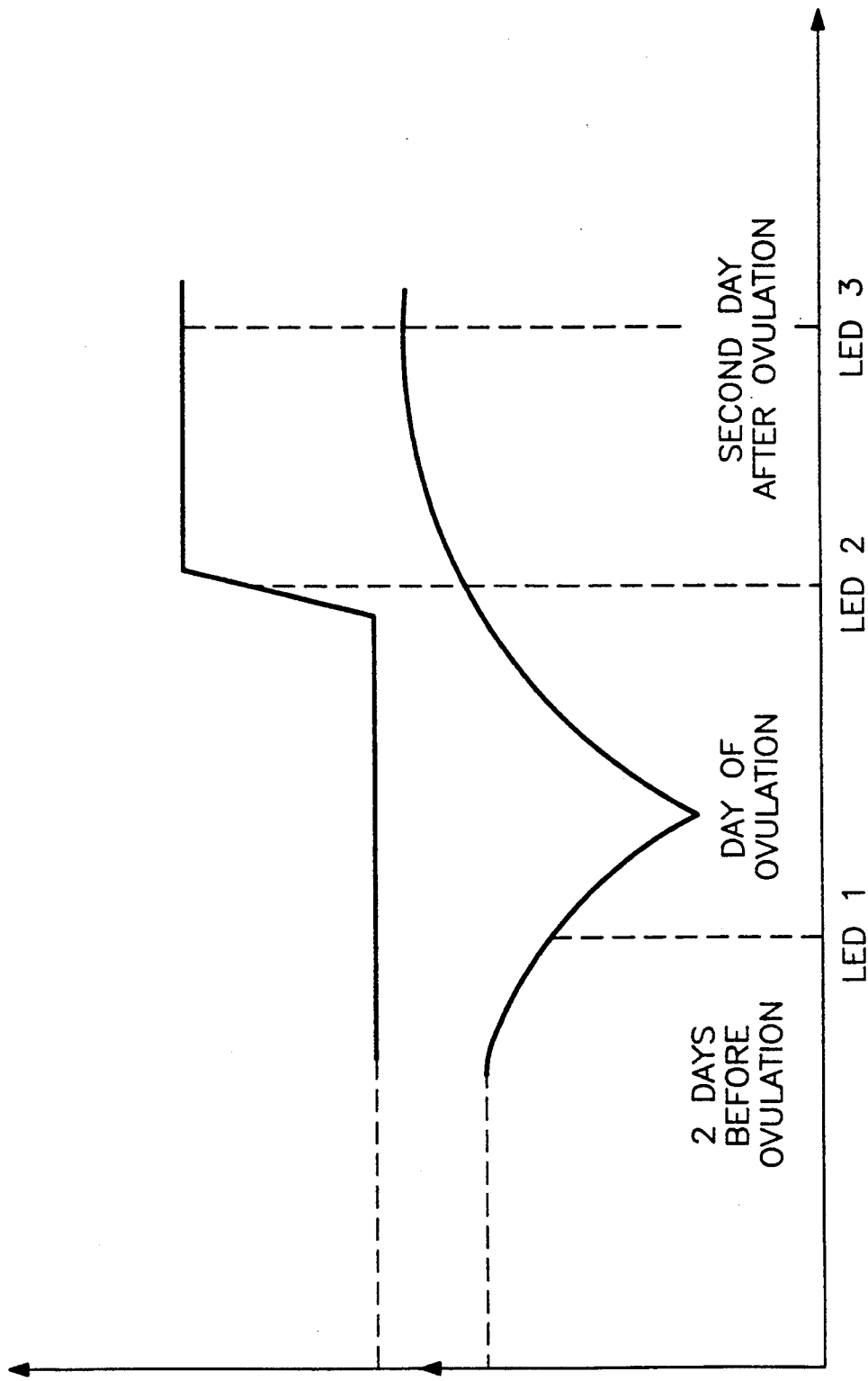
FIG. 9 illustrates the operation of the device of FIG. 7 during the monthly cycle, indicating which of the LEDs will be lit during specific periods of the cycle.

A typical curve obtained by means of such a device is shown in FIG. 9, but this is not displayed and its use is to actuate at the appropriate time the correct LED or any kind of indication—numerical, bar graph—which can be displayed on an LCD display. Output signals of this device will not exceed 15 mVolts Peak to Peak AC in a frequency range of 10 KHz to 100 KHz in constant current which does not exceed 50 $\mu$Amp between the two stainless steel electrodes. The batteries of this apparatus can be in the range of 1.5-6 Volts DC.

Algorithm Software: The software of the device is based upon statistical measurements which were conducted on a test group of subjects. Automatic levelling procedure is a part of the software. This is in order to eliminate the differences between users. A drop of 10–15% from the baseline will give indication of at least 72 hours before ovulation. In order to strengthen this early warning, software is calculating in parallel the rhythm method and will display first indications, whatever comes first as an early warning. After confirmation of the two parameters, the display signal will indicate this.

After the software has recognized the nadir day, it will start to in after dictate that fertile phase is starting to pass.

In parallel, software is used to check temperature changes. When a count of three days of rising temperature is indicated and at the same time the polarization impedance is on a constant rise, then on the fourth day the indication signal of fertile phase will turn off and a new signal indicating infertile phase will start.

Figure 10:
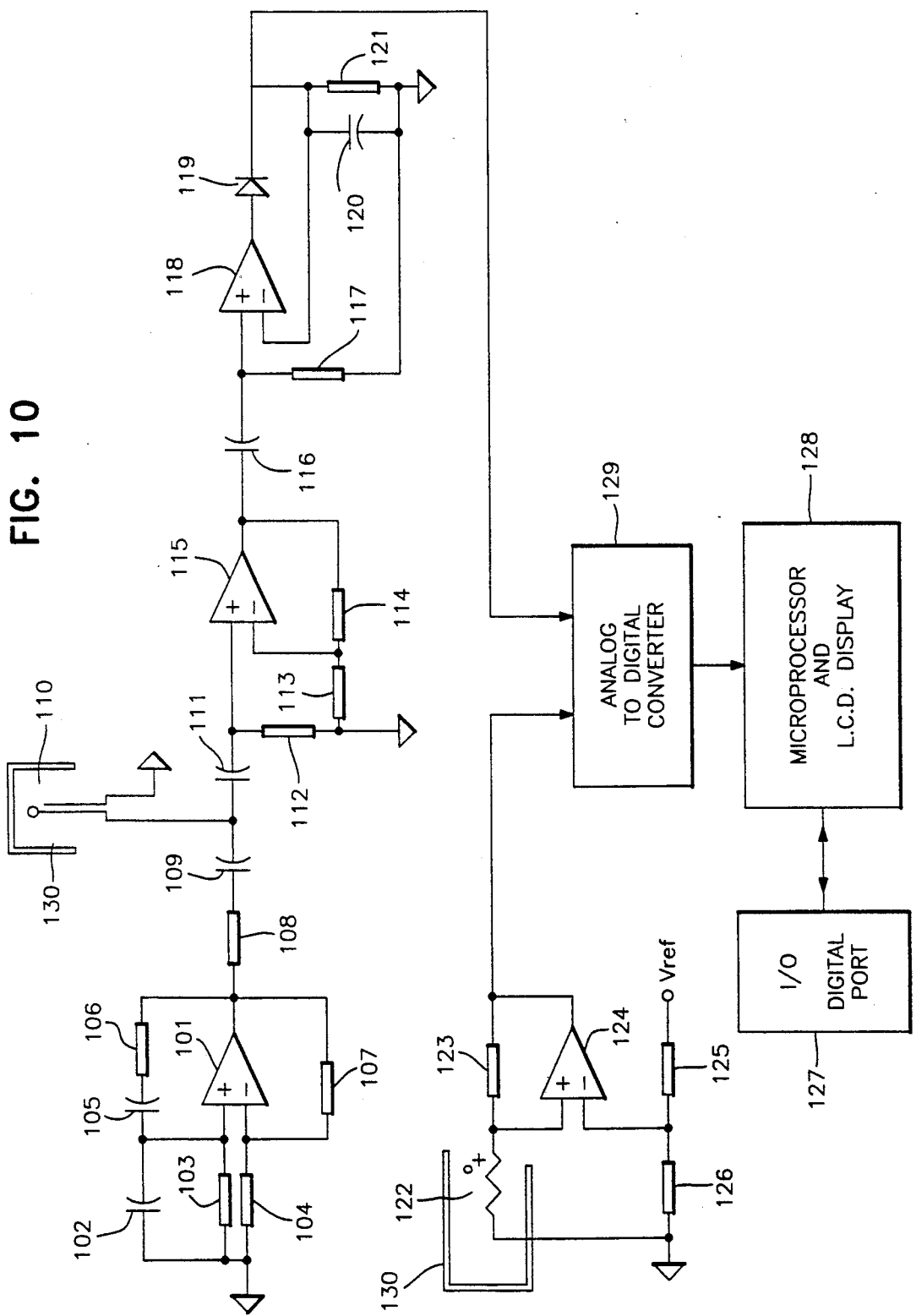
FIG. 10 is a wiring diagram of a device of the present invention, its components being indicated in Table 1.

Legend to FIG. 10

| No. | Device | Circuit | Use |
|-----|--------|---------|-----|
| 101 | Op. Amp | Oscillator | Amplifier |
| 102 | Capacitor | Oscillator | Timing |
| 103 | Resistor | Oscillator | Timing |
| 104 | Resistor | Oscillator | Gain |
| 105 | Capacitor | Oscillator | Timing |
| 106 | Resistor | Oscillator | Timing |
| 107 | Resistor | Oscillator | Gain |
| 108 | Resistor | Oscillator | Output Current Control |
| 109 | Capacitor | Oscillator | D.C. reject |
| 110 | Inp. probe | Z sensor | Sensor |
| 111 | Capacitor | A.C. Amp. | High Pass |
| 112 | Resistor | A.C. Amp. | High Pass |
| 113 | Resistor | A.C. Amp. | Gain |
| 114 | Resistor | A.C. Amp. | Gain |
| 115 | Op. Amp | A.C. Amp. | Amplifier |
| 116 | Capacitor | Rectifier cir. | Coupling |
| 117 | Resistor | Rectifier cir. | Coupling |
| 118 | Op. Amp | Rectifier cir. | Amplifier |
| 119 | Diode | Rectifier cir. | Rectification |
| 120 | Capacitor | Rectifier cir. | Averaging |
| 121 | Resistor | Rectifier cir. | Averaging |
| 122 | NIC resistor | Temp. Meas. | Temperature sensor |
| 123 | Resistor M.F. | Temp. Meas. | Reference resistor |
| 124 | Op. Amp | Temp. Meas. | Amplifier |
| 125 | Resistor | Temp. Meas. | Zero Temp. Set. |
| 126 | Resistor | Temp. Meas. | Zero Temp. Set. |
| 127 | Dig. Interface | I/O Port | Communication |
| 128 | Dig. Interface | Alu and Display | Central Control |
| 129 | A/D Converter and | MPXR | Converter of Z.T. to Dig. |
| 130 | Vagina | Female | Sensed DEVICE |

I claim:

1. A device for detecting the fertile period in a woman's menstrual cycle, said device comprising:
   a probe having an elongated probe body for insertion into the woman's vagina and mucus contained therein, a fist ring-shaped electrode circumferentially surrounding said probe body, a second ring-shaped electrode also circumferentially surrounding said probe body but displaced longitudinally down the probe body from said first ring-shaped electrode, and a distally located temperature sensor for sensing mucus temperature;
   a current generating means electrically connected to said probe, for generating an electrical alternating current not exceeding 50 micro-amperes between said first ring-shaped electrode and said second ring-shaped electrode, and passing through said mucus to thereby effect a voltage indicative of the electrode-to-mucus polarization impedance;
   means for amplifying said voltage indicative of the electrode-to-mucus polarization impedance, said amplifying means having first and second inputs electrically connected to the first and second ring-shaped electrodes, respectively;
   means electrically connected to the output from said amplifying means, for rectifying the output from said amplifying means;
   signal conditioning means electrically connected to said temperature sensor for conditioning the output form said temperature sensor;
   analog-to-digital converting means electrically connected and responsive to the output form said rectifying means to output a signal indicative of the electrode-to-mucus polarization impedance, and also electrically connected and responsive to the output from said signal conditioning means to output a signal indicative of mucus temperature;
   a microprocessor connected and responsive to the signals output by said analog-to-digital converting means, said microprocessor being programmed with an algorithm relating to the woman's menstrual cycle for detecting the approach of ovulation based upon a 10 to 15 percent drop from baseline in the magnitude of said signal indicative of the electrode-to-mucus polarization impedance, for detecting the most fertile day of ovulation and for detecting when ovulation has recently elapsed, the signal indicative of mucus temperature being used to confirm at least one of the detections, said microprocessor including means for outputting a resulting signal indicative of whether ovulation is approaching, is present, or has recently elapsed; and
   a display responsive to the resulting signal form said microprocessor for indicating when ovulation is approaching, when ovulation is present, and when ovulation has recently elapsed.

2. The device of claim 1, wherein said current generating means includes:
   an operational amplifier having positive and negative input terminals and an output terminal;
   a first resistor and a first capacitor electrically connected in series form said positive input terminal to said output terminal;
   a second resistor and a second capacitor electrically connected in parallel from said positive input terminal, through a third resistor, to said negative input terminal;
   a fourth resistor electrically connected from said negative input terminal to said output terminal; and
   a third capacitor and a fifth resistor electrically connected in series from said out-put terminal to said probe.

3. The device of claim 1, wherein said amplifying means comprises:
   an operational amplifier having first and second input terminals and an output terminal;
   a first capacitor for filtering out low frequency signals, said first capacitor being electrically connected from said probe to said positive input terminal;
   first and second resistors electrically connected in series from said positive input terminal to said negative input terminal; and
   a third resistor electrically connected from said negative input terminal to said output terminal, for determining the gain of said operational amplifier.

4. The device of claim 1, wherein said rectifying means comprises:
   an operational amplifier having positive and negative input terminals and an output terminal;
   a diode having an anode electrically connected to the output terminal and a cathode electrically connected t the analog-to-digital converting means;
   a first capacitor electrically connected from said positive input terminal to the output of said amplifying means; and
   a first resistor and second capacitor electrically connected in parallel with respect to one another, and electrically connected in series with a second resistor from the positive input terminal to the cathode of said diode.

5. The device of claim 1, wherein said temperature sensor comprises an NIC resistor.

6. The device of claim 5, wherein said signal conditioning means comprises:

an operational amplifier having positive and negative input terminals and an output terminal, said output terminal being electrically connected to the analog-to-digital converting means;

a reference resistor electrically connected from said negative input terminal to said output terminal;

a first zero temperature setting resistor electrically connected in series with said NIC resistor from said negative input terminal to said positive input terminal; and a second zero temperature setting resistor electrically connected for the positive input terminal to a reference voltage.

7. The device of claim 1, and further comprising an input and output port electrically connected to the microprocessor for communicating therewith.

8. The device of claim 1, wherein said display comprises at least three light-emitting diodes, each light-emitting diode indicating a different period in the menstrual cycle, a first of said At lest three light-emitting diodes corresponding to a first predetermined period before ovulation, a second of said at least three light-emitting diodes corresponding to ovulation, and a third of said at lest three light-emitting diodes corresponding to a second predetermined period faster ovulation fertile period.

9. The device of claim 8, wherein each of said at least three light-emitting diodes emits light having a different color from that of the other light-emitting diodes.

* * * * *